United States Patent
Pernot

(10) Patent No.: US 7,156,659 B2
(45) Date of Patent: Jan. 2, 2007

(54) CONTRA-ANGLE HANDPIECE FOR ROTARY SURGICAL INSTRUMENTS, IN PARTICULAR IN DENTAL SURGERY

(75) Inventor: Jacques Pernot, Vieilley (FR)

(73) Assignee: Micro-Mega International Manufactures, Besancon (FR)

( * ) Notice: Subject to any disclaimer, the term of this patent is extended or adjusted under 35 U.S.C. 154(b) by 92 days.

(21) Appl. No.: 10/514,754

(22) PCT Filed: Apr. 3, 2003

(86) PCT No.: PCT/FR03/01057

§ 371 (c)(1),
(2), (4) Date: Nov. 17, 2004

(87) PCT Pub. No.: WO03/105713

PCT Pub. Date: Dec. 24, 2003

(65) Prior Publication Data

US 2005/0158689 A1    Jul. 21, 2005

(30) Foreign Application Priority Data

Jun. 12, 2002  (FR) .................................. 02 07182

(51) Int. Cl.
*A61C 1/08* (2006.01)
*A61C 1/12* (2006.01)

(52) U.S. Cl. ...................................... 433/114; 433/133

(58) Field of Classification Search ................ 433/112, 433/103, 114, 131, 133
See application file for complete search history.

(56) References Cited

U.S. PATENT DOCUMENTS

| 4,278,428 | A | * | 7/1981 | Straihammer et al. ...... 433/105 |
| 4,406,621 | A | * | 9/1983 | Bailey ........................ 433/126 |
| 6,042,377 | A | * | 3/2000 | Ito ............................. 433/126 |
| 6,245,086 | B1 | | 6/2001 | Storz |
| 2002/0009690 | A1 | | 1/2002 | Kuhn et al. |

FOREIGN PATENT DOCUMENTS

| DE | 938438 | 2/1956 |
| FR | 1243246 | 10/1960 |
| GB | 218792 | 7/1924 |

\* cited by examiner

*Primary Examiner*—Cary E. O'Connor
(74) *Attorney, Agent, or Firm*—Gary M. Cohen

(57) ABSTRACT

A driven appliance, such as a contra-angle handpiece for surgical instruments, in particular for dental surgery, includes a handle, a neck and a head for receiving an instrument. The handle and the neck of the contra-angle handpiece each receive a drive shaft, respectively, an input shaft and an output shaft, which are linked to each other by a gear train. The input shaft and the output shaft are slidingly mounted in their respective bodies, which forms a sheath for the two shafts. The shafts are maintained and supported on stops arranged on the corresponding sheathes through a single elastic element which is housed in the bend linking the handle to the neck.

15 Claims, 1 Drawing Sheet

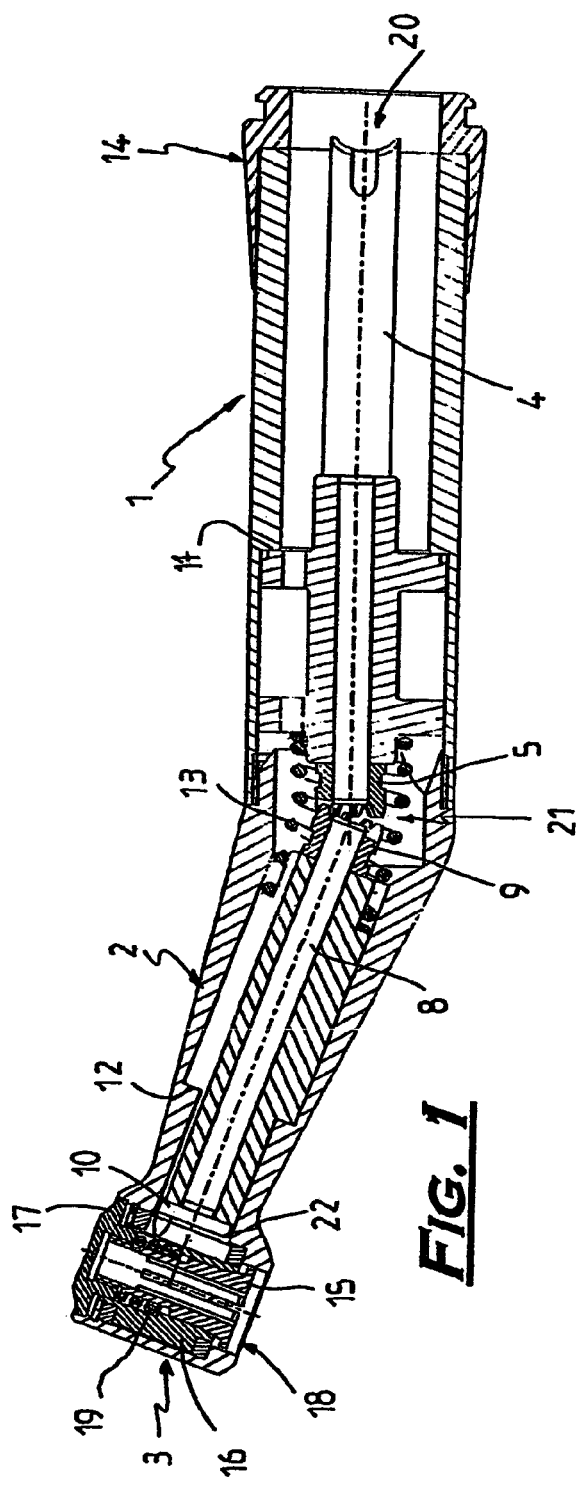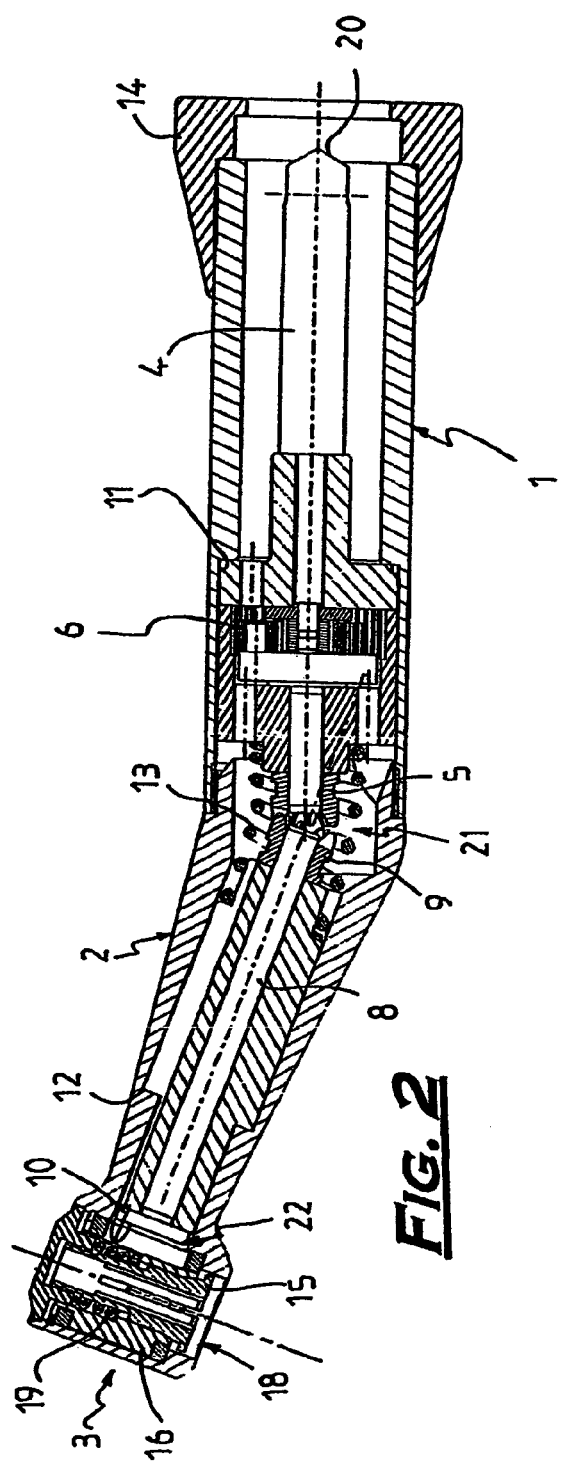

CONTRA-ANGLE HANDPIECE FOR ROTARY SURGICAL INSTRUMENTS, IN PARTICULAR IN DENTAL SURGERY

BACKGROUND OF THE INVENTION

The present invention concerns an improvement to drive apparatus, generally referred to as contra-angle handpieces, for rotary tools used in surgery, and in particular, in dental surgery.

Such contra-angle handpieces are generally made up of an anterior part or "neck" having a cylindrical and/or conical external shape, for supporting the head which is to receive the dental instrument, and a posterior part or "handle" having a shape which is substantially cylindrical and/or conical in revolution.

The handle includes a mechanical connection to a dental drive motor. At the opposite end from the connection to the motor, the handle is connected to the neck of the contra-angle handpiece.

The neck has an axis which intersects with the axis of the handle, and which is positioned at approximately 20 degrees relative to the axis of the handle, in such a way as to form a bend or contra-angle. The axis of the dental instrument is perpendicular to the axis of the neck, and the dental tool is generally oriented in the direction of the axis of the handle.

The assembly comprised of the handle, the neck and the head contains a kinematic chain, the object of which is to transmit rotation of the motor's shaft to the dental instrument. This can possibly include a reduction or multiplication of the speed of rotation of the dental instrument.

In view of the above-described angle, and contra-angle structure, the kinematic chain is also made up of three parts. A first part is arranged in the handle, a second part is arranged in the neck, and a third part is arranged in the head. The third part of the kinematic chain is also equipped with removable or non-removable means for fixing a dental instrument to the handle, for driving the dental instrument in rotation and for stopping translational movement of the instrument along the axis of the head.

Generally speaking, rotational movement is transmitted between these different parts by gears having non-parallel axes. The position of these non-parallel axes is of great importance, on the one hand, in terms of the useful life of the contra-angle handpiece (poor positioning being reflected in premature wear of the pinions) and, on the other hand, in terms of comfort for the patient and for the dental surgeon (poor positioning being reflected in excessive noise). This is particularly so in view of the fact that the speeds of rotation are presently 40,000 rpm.

Thus, the positioning of each part of the kinematic chain is generally such that each of the parts is fixed in the respective parts of the contra-angle handpiece (handle, neck, head) so as to form an integral body, in this way constituting an independent sub-unit.

Although such apparatus are satisfactory, the means of fixing the elements of the kinematic chain are complex. Consequently, restoration of the components by replacing them is virtually impossible for non-specialists.

SUMMARY OF THE INVENTION

The object of the present invention is to provide an improvement to such apparatus which solves all, or at least some of the aforementioned disadvantages, by proposing an economical solution for assembly of the kinematic chain which also, where appropriate, allows components to be restored by replacement by non-specialists.

To this end, the present invention is directed to a drive apparatus, referred to as a contra-angle handpiece, for rotary tools used in surgery, and in particular in dental surgery. The contra-angle handpiece is comprised of a handle, a neck, and a head, and a tool is fixed in the head. Both the handle and the neck of the contra-angle handpiece receives, in its interior, a drive shaft (hereafter designated, respectively, as an input shaft for the handle and as an output shaft for the neck). The input shaft and the output shaft are connected to one another by a gear train, and are slidingly mounted in their respective bodies, forming a sleeve for such structures. The input shaft and the output shaft are maintained and supported on an abutment, arranged on the corresponding sleeve, by a single elastic element which is housed in the bend connecting the handle to the neck.

According to an advantageous characteristic of the present invention, the elastic element is formed by a compression spring mounted coaxially with respect to the gear train, one end of which bears on the input shaft, and the other end of which bears on the output shaft.

According to another advantageous characteristic of the present invention, the handle of the apparatus is additionally formed as a cylindrical body, and a removable and interchangeable connection piece is arranged on the cylindrical body, permitting connection to the drive motor with different types of connectors.

According to another advantageous characteristic of the present invention, the head of the apparatus is equipped with a quick-coupling system for receiving the tool. In one embodiment, the quick-coupling system for the tool includes a clamp made of an elastic plastic material. The free end of the clamp is able to open, like a corolla, by way of longitudinal grooves formed across a major part of its body. A frustoconical widening is provided at the outer periphery of the clamp to cooperate with a cylindrical sleeve mounted inside the body of the head. An opposite end of the clamp is fixed, by way of a threaded connection, to a push-button which is axially movable and which is returned to its rest position by a spring. This ensures, upon return of the push-button, that the clamp is tightened and, consequently, that the tool is fixed to the head. The spring bears on a rotating cylindrical sleeve made of a plastic material.

According to another advantageous characteristic, the cylindrical sleeve of the quick-coupling system includes a drive member which meshes with a crankpin integral with the output shaft. This ensures that rotational movement of the motor is converted into an alternating rotational movement of the tool.

According to another advantageous characteristic, the body of the neck and the body of the handle are made of plastic and are connected to one another by a releasable fixing means (of the threaded type). In an alternative embodiment, the body of the neck and the body of the handle are connected to one another by welding.

The above-mentioned characteristics of the present invention, and others, will become clearer from a reading of the description of alternative embodiments which is provided below, with reference to the following drawings.

BRIEF DESCRIPTION OF THE DRAWINGS

FIG. 1 is a longitudinal cross-section taken through a contra-angle handpiece produced in accordance with the present invention.

FIG. 2 is a longitudinal cross-sectional view, similar to FIG. 1, illustrating an alternative embodiment of the present invention.

DETAILED DESCRIPTION OF PREFERRED EMBODIMENTS

FIGS. 1 and 2 illustrate a dental contra-angle handpiece comprised of a handle 1, a neck 2 and a head 3. A tool (not shown) is fixed in the head 3. Interior portions of the handle 1, the neck 2 and the head 3 of the contra-angle handpiece each receive one or more elements of a kinematic chain for transmitting the rotational movement of a motor to the tool which is to be driven.

The handle 1 receives, for example, an assembly including a drive shaft (the input shaft 4). One end of the input shaft 4 engages the drive shaft (not shown) of the motor. The other end of the input shaft 4 has a driving pinion 5 which transmits rotation to the kinematic element of the neck 2. Speed reduction or multiplication elements 6 can be provided between the pinion 5 and the input shaft 4, as can be seen from FIG. 2.

The neck 2 receives a transmission shaft (the output shaft 8). One end of the output shaft 8 is provided with a driven pinion 9 which meshes with the driving pinion 5 of the input shaft 4 of the handle 1. The other end of the output shaft 8 has a member for transmitting movement to the head 3. The movement transmitting member is preferably of the crankpin type 10. Alternatively, the movement transmitting member can be a pinion or a friction wheel.

In accordance with the present invention, the input shaft 4 and the output shaft 8 of the apparatus are slidably mounted in their respective bodies, which form a sleeve for the assembly. The input shaft 4 and the output shaft 8 are respectively supported on an abutment 11, 12, each arranged on their corresponding sleeves, and are coupled by a single elastic element 13 housed in a bend which connects the handle 1 to the neck 2. Such an elastic element 13 advantageously guarantees correct positioning of the transmission elements of the kinematic chain.

It will be noted that the body of the neck 2 and the body of the handle 1 are made of plastic material. The body of the neck 2 and the body of the handle 1 are connected to one another by a releasable connection, such as the threaded connection illustrated in the figures, or as an alternative, are welded to one another.

The elastic element 13 is formed, for example, by a compression spring which is mounted coaxially with respect to the driving pinion 5 and the driven pinion 9 forming the gear train of the apparatus. One end of the compression spring bears on the input shaft 4, and the other end of the compression spring bears on the output shaft 8, as is illustrated in the figures.

In addition, the handle 1 of the apparatus is advantageously formed by a cylindrical body. A removable and interchangeable connection piece 14 is arranged on the cylindrical body to permit a connection to the drive motor using different types of connectors, as can be seen in the figures.

The head 3 of the apparatus is additionally provided with a quick-coupling system for engaging the tool. The quick-coupling system is formed by a clamp 15, which is made of an elastic plastic material. The clamp 15 has a free end which is able to open, like a corolla, along longitudinal grooves which are formed over major portions of its body, and a frustoconical widening at its outer periphery which is intended to cooperate with a cylindrical sleeve 16 mounted inside the body of the head 3. At the opposite end, the clamp 15 is fixed, by threaded engagement, to a push-button 17. The push-button 17 is axially movable, and is returned to its rest position by a spring 19. The spring 19 ensures that, on return of the push-button 17, the clamp 15 is tightened, and consequently, that the tool is fixed in the head 3 when introduced through an opening 18 which is formed in the head 3 at the end remote from the push-button 17. The spring 19 bears on the rotating cylindrical sleeve 16, which is made of a plastic material.

The cylindrical sleeve 16 additionally includes a drive member which meshes with the driven crankpin 10 which is integral with the output shaft 8, thereby ensuring that the rotational movement of the motor is converted into an alternating rotational movement of the tool.

Operation of the drive apparatus (i.e., the contra-angle handpiece) for rotary tools used in surgery, particularly in dental surgery, will be evident from the foregoing description, and will now be explained in detail.

The apparatus (the contra-angle handpiece) is connected to a drive motor by the appropriate connection piece 14. A first drive train 20 drives the input shaft 4 of the handle 1. A second drive train 21 is driven by the input shaft 4, and drives the output shaft 8 of the neck 2. Finally, a third drive train 22 is driven by the output shaft 8, for operating a rotary tool which is received in the clamp 15 which is mounted in the head 3 of the apparatus.

The elastic element 13 is arranged coaxially with respect to the second gear train 21 and ensures correct positioning of the input shaft 4 and of the output shaft 8 of the apparatus, against each of the abutments 11, 12. The abutments 11, 12 are mounted on the body of the handle 1 and on the body of the neck 2, facing each other in such a way that the shafts 4, 8 can be fit in their respective bodies 1, 2 only along the region of the bend of the apparatus, namely, along the handle/neck connection.

It will be appreciated from the foregoing that the apparatus of the present invention is relatively simple to produce, and permits power transmission using elements which are economical in design and which are easier to assemble compared to conventional contra-angle handpieces. In addition, such simplification affords the possibility, where necessary, of replacing used or defective parts by exchanging them, without the need for this to be done by specialists.

Although the invention has been described in connection with two particular embodiments, the present invention will encompass all technical equivalents of the means described.

The invention claimed is:

1. A drive apparatus for a rotary tool used in surgery, including dental surgery, comprising:
   a handle;
   a neck linked with the handle by a connection;
   a head coupled with the neck, for receiving the rotary tool;
   wherein the handle has an interior which receives an input drive shaft, the neck has an interior which receives an output drive shaft, and the input drive shaft is connected to the output drive shaft by a gear train;
   wherein the input drive shaft is slidingly mounted in the interior of the handle and the output drive shaft is slidingly mounted in the interior of the neck, forming a sleeve for the input drive shaft and the output drive shaft;
   abutments formed on the interior of the handle and on the interior of the neck; and
   an elastic element housed in the connection linking the handle and the neck, for maintaining and supporting the input drive shaft and the output drive shaft on the abutments, wherein the elastic element is formed by a compression spring mounted coaxially with respect to the gear train so that one end of the compression spring bears on the input drive shaft and so that another end of the compression spring bears on the output drive shaft.

2. The drive apparatus of claim 1 wherein the drive apparatus is a contra-angle handpiece.

3. The drive apparatus of claim 2 wherein the connection includes a bend forming a contra-angle.

4. The drive apparatus of claim 1 which includes a single elastic element.

5. The drive apparatus of claim 1 wherein the handle is formed as a cylindrical body, and wherein the handle further includes a removable and interchangeable connection piece arranged on the handle to permit a connection of the handle with different types of drive motor connectors.

6. The drive apparatus of claim 1 wherein the head further includes a quick-coupling system for receiving the tool.

7. The drive apparatus of claim 6 wherein the quick-coupling system includes a clamp having a free end which is capable of being opened and a frustoconical widening at an outer periphery of the clamp, a cylindrical sleeve mounted inside the head, for cooperating with the clamp, and a push-button coupled with an opposite end of the clamp which is axially movable and returnable to a rest position by a spring which bears on the cylindrical sleeve.

8. The drive apparatus of claim 7 wherein the clamp has a body, and wherein the free end of the clamp has longitudinal grooves formed across major portions of the body of the clamp, for opening the clamp.

9. The drive apparatus of claim 7 wherein the clamp is formed of an elastic plastic material.

10. The drive apparatus of claim 7 wherein the spring operates to return the push-button to a rest position for tightening the clamp and for fixing the tool in the head.

11. The drive apparatus of claim 7 wherein the cylindrical sleeve is made of a plastic material.

12. The drive apparatus of claim 7 wherein the cylindrical sleeve further includes a drive member which meshes with a crankpin which is integral with the output drive shaft, for converting rotational movement of a drive motor for operating the drive apparatus into an alternating rotational movement for operating the tool.

13. The drive apparatus of claim 1 wherein the neck has a body and the handle has a body, and wherein the body of the handle and the body of the neck are made of a plastic material.

14. The drive apparatus of claim 13 wherein the body of the neck and the body of the handle are connected by a releasable threaded connection.

15. The drive apparatus of claim 13 wherein the body of the neck and the body of the handle are connected by a welded connection.

\* \* \* \* \*